United States Patent [19]

Yanagawa

[11] Patent Number: 5,574,006
[45] Date of Patent: Nov. 12, 1996

[54] NASALLY ADMINISTRABLE PEPTIDE COMPOSITIONS ON HYDROXYAPATITE CARRIERS

[75] Inventor: Akira Yanagawa, Yokohama, Japan

[73] Assignee: Dott Research Laboratory, Yokohama, Japan

[21] Appl. No.: 325,652

[22] Filed: Oct. 18, 1994

[30] Foreign Application Priority Data

Oct. 19, 1993 [JP] Japan .................................. 5-284423
Jun. 15, 1994 [JP] Japan .................................. 6-155456

[51] Int. Cl.$^6$ .......................... A61K 9/14; A61K 38/23; A61K 38/28; A61K 47/02
[52] U.S. Cl. .................. 514/3; 424/499; 514/2; 514/12; 514/21; 514/770; 519/784; 519/951; 519/970
[58] Field of Search ................. 424/94.1, 94.3, 424/499, 602; 514/2, 3, 12, 21, 770, 951, 784, 970, 971, 972

[56] References Cited

U.S. PATENT DOCUMENTS

| | | | |
|---|---|---|---|
| 4,371,523 | 2/1983 | Grodsky et al. | 514/3 |
| 5,009,898 | 4/1991 | Sakuma et al. | 424/491 |
| 5,055,307 | 10/1991 | Tsuru et al. | 424/497 |
| 5,116,729 | 5/1992 | Ismail et al. | 435/25 |
| 5,478,578 | 12/1995 | Arnold et al. | 424/499 |

FOREIGN PATENT DOCUMENTS 180707 7/1990 Japan .
255095 10/1993 Japan .

OTHER PUBLICATIONS

Translation of Japan Kokai 2–180707, "Method For Manufacturing Particle Aggregate of Phosphoric Acid Compound" (13 Jul. 1990).
Green et al, Perry's Chemical Engineers' Handbook, 6th ed., published 1984 by McGraw–Hill Book Co. (NY), p. 21–15.
Bull. Tokyo Med. Dent. Univ., vol. 25, issued 1978, Kuboki et al, "Hydroxyapatite–Reactive Salivary Protein . . . ", pp. 123–131.
Bio–Medical Materials and Engineering, vol. 4, No. 4, issued 1994, Kano et al, "Application of Hydroxyapatite Sol . . . ", pp. 283–290.
Proc. Am. Assoc. Cancer Res., vol. 35, issued Mar. 1994, Mizuno et al, "Intraperitoneal Administration of Hydroxyapatite . . . ", p. 418, Abs. No. 2491.

*Primary Examiner*—Jeffrey E. Russel
*Attorney, Agent, or Firm*—Foley & Lardner

[57] ABSTRACT

A physiologically active peptide composition having a physiologically active peptide dispersed homogeneously in and adsorbed homogeneously onto a unique carrier. The physiologically active peptide composition contains a physiologically effective amount of the physiologically active peptide dispersed homogeneously in and adsorbed homogeneously onto hydroxyapatite. The composition is nasally administrable in powdery form.

7 Claims, No Drawings

NASALLY ADMINISTRABLE PEPTIDE COMPOSITIONS ON HYDROXYAPATITE CARRIERS

BACKGROUND OF THE INVENTION

1. Field of the Invention

The present invention relates to a physiologically active peptide composition and, more particularly, to a physiologically active peptide composition containing a physiologically active peptide such as a peptide hormone, a physiologically active protein or an enzymatic protein and having high stability in the form of a preparation and improved absorbability into the body, for example, when administered nasally.

2. Description of the Prior Art

Physiologically active peptides such as calcitonin and insulin are polymers which are extensively employed in therapeutical treatment for various medical usage due to their specific physiological activity.

These physiologically active peptides, however, can little be absorbed intact from the mucous membrane of the intestine because they are likely to be decomposed with proteases existing in the digestive system or are high in molecular weight and polarity. Hence, they cannot be administered orally and they can be administered only through injection. The injectable administration cannot be said to be preferable because the injection causes pain at the site of injection to patients. In addition, particularly, when the injection should be repeated at constant intervals, such pain is repeated whenever they are injected and it may often become too severe for patients to endure. Therefore, strong demand has been made to develop a method for administering the physiologically active peptide via a non-injection route and, more preferably, a method which enable patients to administer it by themselves, which further should be safe, simple in administration and administrable with less frequency.

As one of such methods for administering the physiologically active peptides, an aerosol in the form of a suspension, which uses a fluorinated hydrocarbon as a spouting agent, has been developed for nasally administering, for example, calcitonin. As another means for nasal administration, a spraying agent has been proposed as a nasally administrable liquid preparation, which is a preparation in which calcitonin is formulated with a surface-active agent as an absorption promoter. Furthermore, recently, there have been proposed some nasally administrable powdery preparations having improved absorbability, which are prepared by adsorbing calcitonin onto a polysaccharide such as cellulose. The various techniques for nasal administration, which have recently been actively developed, are said to be in principle superior as methods for administering such physiologically active peptides as unlikely to be administered orally. Since the plexus venosus develops at the nasal lamina propria mucosae of the nasal cavity, the physiologically active peptide, when administered nasally, is absorbed through the mucous membrane of the nasal cavity into the circulatory system of the body; however, nasally administrable preparations so far proposed are not satisfactory because of poor absorbability of the physiologically active peptide or local irritation so that they are not commercially available yet.

SUMMARY OF THE INVENTION

The present invention has the object to provide a nasally administrable composition to nasally administer such a physiologically active peptide as unlikely to be administered orally, with higher bioavailability and less irritation than those of other nasally administrable preparations so far proposed.

As a result of extensive studies and research on such nasally administrable preparations to achieve the object of the present invention, the present inventor has found that a composition, which is prepared by homogeneously dispersing the physiologically active peptide, such as calcitonin or insulin, in a unique carrier that has not yet been studied as a carrier for use with a nasally administrable preparation and by homogeneously adsorbing it onto the carrier, is administrable via a nasal route—in other words, that the composition can be applied to the mucous membrane of the nasal cavity—to thereby allow a clinically effective treatment.

In other words, it has been found by the present inventor that the bioavailability is attainable to such an extent as being equal to or higher than that gained by standard injection administration, by the technology that involves homogeneously dispersing the physiologically active peptide such as calcitonin in a unique carrier and adsorbing said peptide onto the carrier.

The present invention has been completed on the basis of these findings.

As described hereinabove, the primary object of the present invention is to provide a carrier for a nasally administrable composition, more particularly, to provide a carrier which is composed of finely divided particles of hydroxyapatite having a mean particle size ranging from 20 µm to 250 µm.

Active substances to be contained in the composition may include all of the active substances which may be used for nasal administration; however, physiologically active peptides are preferred.

The second object of the present invention is to provide a physiologically active peptide composition and, more particularly, to provide a composition prepared by homogeneously dispersing a physiologically effective amount of the physiologically active peptide in hydroxyapatite having a mean particle size ranging from 20 µm to 250 µm and adsorbing said peptide thereonto homogeneously.

In other words, most specific object of the present invention is to provide a physiologically active peptide composition comprising a physiologically active peptide and hydroxyapatite, wherein a physiologically effective amount of said physiologically active peptide is dispersed homogeneously in and adsorbed homogeneously onto hydroxyapatite whose mean particle size ranges from 20 µm to 250 µm, which is nasally administrable in the form of a powdery preparation.

Other objects, features and advantages of the present invention will become apparent in the course of the description of the preferred embodiments.

DETAILED DESCRIPTION OF THE INVENTION

Hydroxyapatite, the carrier used in the present invention, is a main component of inorganic materials in hard tissues such as bones or tooth roots, and it is used for coating substance of implants for bones, joints and tooth roots so far.

It should be noted herein, however, that nothing has been so far reviewed about the applicability to a carrier for nasally administrable preparation and the present inventor first discovered that hydroxyapatite is employable as a carrier for a nasally administrable preparation.

Further, it has been found by the present inventor that hydroxyapatite having a mean particle size ranging from 20 µm to 250 µm to be used as the carrier for the composition of the present invention offers the effect of promoting the absorption of the physiologically active peptide into the body.

For nasally administrable preparations, it has been thought so far that a water-soluble carrier would help to attain a good absorption of the active substance into the body. However, the present inventor found that an excellent absorption of active substances is obtainable by homogeneously dispersing the active substance in a water-insoluble carrier, for example, hydroxyapatite, and homogeneously adsorbing said active substance thereonto.

The hydroxyapatite used in the present invention includes synthetic hydroxyapatite and hydroxyapatite obtained from organisms (bio-hydroxyapatite). The bio-hydroxyapatite may be prepared by using bones or teeth of animals from which organic materials are removed.

The physiologically active peptide composition according to the present invention is prepared by homogeneously dispersing a physiologically effective amount of the physiologically active peptide in the unique carrier of the present invention and adsorbing said peptide thereonto.

The physiologically active peptide to be used as an active ingredient of the composition according to the present invention may include a peptide hormone, a physiologically active protein and an enzymatic protein.

The peptide hormones may include, for example, parathormone (parathyroid hormone), calcitonin, insulin, angiotensin, glucagon, gastrin, secretin, growth hormone, prolactin (luteotropic hormone), gonadotropin (gonodotropic hormone), thyrotropic hormone, adrenocorticotropic hormone, melanocyte stimulating hormone, vasopressin, oxytocin, protirelin, luteinizing hormone releasing hormone, corticotropin, somatotropin, thyrotropin (thyroid stimulating hormone), somatostatin (growth hormone inhibiting factor), G-CSF, erythropoietin, superoxide dismutase (SOD), and so on.

In addition, interferon, interleukin, urokinase, lysozyme, vaccine and so on may also be used as the physiologically active peptide.

It is to be noted herein that the physiologically active peptides to be used for the present invention are not restricted to those described hereinabove and that any nasally administrable physiologically active peptide may be formulated into the composition according to the present invention.

Among those physiologically active peptides as described hereinabove, the peptide hormones are preferred. Further, among the peptide hormones, calcitonin, insulin and somatostatin are preferred and calcitonin and insulin are particularly preferred.

The calcitonin to be preferably employed for the composition according to the present invention may include, for example, salmon calcitonin, human calcitonin, hog calcitonin, chicken calcitonin, cattle calcitonin, eel calcitonin, and so on. These calcitonins are naturally occurring ones that are to be extracted from the origin and that are commercially available. It can be noted herein that eel calcitonin is higher in stability than human calcitonin that in turn is higher than salmon calcitonin; however, even the salmon calcitonin relatively low in stability, being homogeneously dispersed in and adsorbed onto the unique carrier to be used for the present invention, can be a physiologically active peptide composition that is high in bioavailability and concentration in blood. Therefore, calcitonins are most suitable as the physiologically active peptide for the present invention.

Hence, one most preferable mode of the composition according to the the present invention is a physiologically active peptide composition in powdery form, which is formulated into a nasally administrable preparation, in which a physiologically effective amount of calcitonin is homogeneously dispersed in and adsorbed onto hydroxyapatite.

Furthermore, the other most preferable mode of the composition according to the present invention is a physiologically active peptide composition in powdery form, which is formulated into a nasally administrable preparation, in which a physiologically effective amount of insulin is homogeneously dispersed in and adsorbed onto hydroxyapatite.

The physiologically effective amount of the physiologically active peptide to be contained in the composition according to the present invention may vary with factors such as the active substance to be chosen, the disease to be treated, desired number of administration, desired effect of therapy, and so on. When administering the composition of the present invention through the nasal cavity, the physiologically effective amount of the physiologically active peptide may be determined on the basis of a comparison of its bioavailability relative to other known preparations cantaining the same active substance.

For example, when insulin is administered subcutaneously to a diabetic patient, the first dose of the insulin usually ranges from 4 insulin unit to 20 insulin unit and the maintenance dose usually ranges from 4 units to 100 units per day, the maximum dose being 800 units per day. Therefore, when administered through nasal route, it is appropriate that the composition be applied at a dose ranging usually from 4 to 100 insulin unit.

Furthermore, when calcitonin, e.g. salmon calcitonin, is administered intramuscularly, a dose ranging from approximately 50 MRC unit (IU) to approximately 100 MRC unit (IU) is applied usually once per day to three times per week. Hence, when administered through nasal route, it is appropriate that the composition be applied at a dose of approximately 50 MRC unit (IU) to approximately 400 MRC unit (IU), preferably from approximately 100 MRC unit (IU) to approximately 200 MRC unit (IU), once per day to three times per week.

The physiologically active peptide composition according to the present invention may contain the physiologically active peptide at a percentage of from approximately 0.005% to approximately 30%, preferably from approximately 0.01% to approximately 20%, more preferably from approximately 0.1% to approximately 5.0%, with respect to the total weight of the preparation.

On the other hand, the physiologically active peptide compositions according to the present invention can achieve high extent of nasal absorption when it contains hydroxyapatite as a carrier at a rate of from 70% to approximately 99.995%, preferably from approximately 80% to approximately 99.99%, more preferably from approximately 95% to approximately 99.9%, with respect to the total weight of the preparation.

For formulation into a powdery preparation of the physiologically active composition according to the present invention, the physiologically active peptide may be admixed with the carrier in a mortar by applying pressure or shear force to the resulting mixture. The hydroxyapatite to be used as the carrier may have a mean particle size ranging from approximately 20 µm to approximately 250 µm, preferably from approximately 30 µm to approximately 60 µm. On the other hand, it is preferred that the physiologically active peptide is pulverized to the smallest possible particles, the mean particle size being smaller than 20 µm, preferably smaller than 10 µm.

By using the composition according to the present invention, a nasally administrable preparation may be made in such a manner as will be described hereinafter. More specifically, when salmon calcitonin or eel calcitonin is used as the physiologically active peptide, a physiologically effective amount of the calcitonin is admixed with an aqueous solution of pH 4.5 to pH 5.5 containing, as a stabilizing agent, gelatin at a rate of, for example, approximately 1% and aspartic acid at a rate of, for example, approximately 0.1% to 0.5%, preferably approximately 0.38%, and the resulting mixture is then freeze-dried. The resulting powdery mixture is then kneaded at a relative humidity of approximately 55% with hydroxyapatite, thereby yielding fine powder of a nasally administrable composition with the physiologically active peptide adsorbed homogeneously onto the hydroxyapatite.

In order to prevent loss of activity of the physiologically active peptide prior to administration, the nasally administrable composition may then be filled in capsules of a low-grease type and packaged in an appropriate form, preferably in a closed form, by combining blister packing with aluminum packaging.

It should be noted that other physiologically active peptides (e.g. insulin) may be likewise treated in substantially the same manner as described hereinabove to thereby yield the composition.

As a result of the tests described hereinafter, it is found that a homogeneous humidity of the tested preparation is preferably approximately 55%. This will be described later.

The specific effects offered by the test examples of the physiologically active peptide compositions according to the present invention are indicated hereinafter.

TEST EXAMPLE 1

A nasally administrable composition in powdery form was prepared by formulating insulin as a physiologically active peptide at the rate of 2.4 mg/rabbit (5 insulin unit (IU)/rabbit) with hydroxyapatite as a carrier having a mean particle size ranging from 30 to 60 µm.

The resulting composition was nasally administered once to six male New Zealand rabbits.

The average fall of the blood sugar was measured and represented in percentage (%) at 0, 15, 30, 60, 120 and 180 minutes after administration.

For comparison, 2 (IU)/rabbit of insulin was administered subcutaneously to six male New Zealand rabbits and the average fall of the blood sugar was measured and represented in parcentage (%) at 0, 60, 120, 240 and 360 minutes after administration.

Table 1 below indicates the average fall of the blood sugar.

TABLE 1

| Nasally form | Average fall of the blod sugar |  |  |  |  |  |
|---|---|---|---|---|---|---|
|  | Time for measurement (minutes) |  |  |  |  |  |
| Present invention | 0 | 15 | 30 | 60 | 120 | 180 |
|  | 100% | 105% | 66% | 67% | 84% | 96% |
| S.C. form |  |  |  |  |  |  |
| Comparison | 0 | 60 | 120 | 240 |  | 360 |
|  | 100% | 57% | 56% | 84% |  | 94% |

As is apparent from Table 1 above, it was found that hydroxyapatite was effective to attain better absorption of insulin through nasal route.

TEST EXAMPLE 2

A nasally administrable composition in powdery form was prepared by formulating salmon calcitonin as a physiologically active peptide at the rate of 200 MRC (IU) per 25 mg with hydroxyapatite as a carrier having a mean particle size ranging from 40 to 45 µm.

The resulting composition was nasally administered once at the dose of 25 mg to six healthy male adults and the blood (2.5 ml) was collected from each of the tested adults prior to administration and then at 5, 10, 15, 20, 30, 45, 60, 90, 120 and 180 minutes after administration. The concentration of the salmon calcitonin in each of the collected blood samples was assayed with a standard RIA assay kit.

Table 2 below indicates the change of concentrations of the salmon calcitonin in the blood.

TABLE 2

| | Concentration of salmon calcitonin in the blood (pg/ml) | | |
|---|---|---|---|
| Sampling time | Concentration of salmon calcitonin in the blood (pg/ml) Case Nos. | | |
| | No. 1 | No. 2 | No. 3 |
| 0 | ~7 | ~7 | ~7 |
| 5 | 55.50 | 14.05 | 76.25 |
| 10 | 93.05 | 44.12 | 107.67 |
| 15 | 49.84 | 77.03 | 118.26 |
| 20 | 65.95 | 59.36 | 95.07 |
| 30 | 21.08 | 47.69 | 102.78 |
| 45 | 12.54 | 24.68 | 60.68 |
| 60 | 13.50 | 19.43 | 42.97 |
| 90 | 7.92 | ~7 | 21.78 |
| 120 | ~7 | ~7 | 12.75 |
| 180 | ~7 | ~7 | ~7 |

As is apparent from Table 2 above, it was found that the composition in powdery form demonstrated a high degree of absorption of the calcitonin into the blood and, as a result, hydroxyapatite was effective to attain better absorption of calcitonin.

TEST EXAMPLE 3

A nasally administrable composition in powdery form was prepared by formulating salmon calcitonin as a physiologically active peptide at the rate of 200 MRC (IU) per 25 mg with hydroxyapatite as a carrier.

The resulting composition was nasally administered once at the dose of 25 mg to six healthy male adults and the blood (2.5 ml) was collected from each of the tested adults prior to administration and then at 5, 10, 15, 20, 30, 45, 60, 90, 120 and 180 minutes after administration. The concentration of the salmon calcitonin in each of the collected blood samples was assayed with a standard RIA assay kit.

Table 3 below indicates the change of concentrations of the salmon calcitonin in the blood.

TABLE 3

Concentration of salmon calcitonin in the blood (pg/ml)

| Sampling time | Concentration of salmon calcitonin in the blood (pg/ml) Case Nos. | | | |
|---|---|---|---|---|
| | No. 4 | No. 5 | No. 6 | No. 7 |
| 0 | ~7 | ~7 | ~7 | ~7 |
| 5 | 65.30 | 66.02 | 57.83 | 72.72 |
| 10 | 98.88 | 95.22 | 83.75 | 130.21 |
| 15 | 96.96 | 106.69 | 91.55 | 139.54 |
| 20 | 59.91 | 102.60 | 63.17 | 122.29 |
| 30 | 46.96 | 71.13 | 48.09 | 91.38 |
| 45 | 23.89 | 57.42 | 30.95 | 45.91 |
| 60 | 14.31 | 33.21 | 19.56 | 15.62 |
| 90 | ~7 | 13.06 | 10.39 | ~7 |
| 120 | ~7 | 8.76 | ~7 | ~7 |
| 180 | ~7 | ~7 | ~7 | ~7 |

As is apparent from Table 3 above, hydroxyapatite was effective to attain better absorption of calcitonin through the nasal cavity, and the maximum concentration of the calcitonin was achieved in a short time after nasal administration.

TEST EXAMPLE 4

Hydroxyapatite (200 mg) having a mean particle size of approximately 40 μm was admixed with salmon calcitonin (5,200 MRC (IU)/mg) having a mean particle size of approximately 15 μm, and pulverized at 4° C. in an agate mortar.

From the powdery mixture, salmon calcitonin unadsorbed on hydroxyapatite was separated and removed and the amount of the salmon calcitonin adsorbed thereon was measured. This was done twice with different samples.

For each sample, approximately 10 mg of the powdery mixture was weighed precisely in a glass vessel and to this mixture was added 0.1M acetic acid water solution containing 1% bovine serum albumin (BSA) to make the total amount 100 ml. Then the amount of the salmon calcitonin was measured by salmon calcitonin RIA method. The results are shown in Table 4 below.

TABLE 4

| Case Nos. (Carrier) | Amount of salmon Calcitonin | |
|---|---|---|
| | ng/mg | MRC/mg |
| No. 1 (hydroxyapatite) | 1,780 | 9.79 |
| No. 2 (hydroxyapatite) | 2,590 | 14.2 |

Table 4 above shows that hydroxyapatite used as the carrier demonstrated a high degree of the effect of adsorbing the physiologically active peptide, that is, calcitonin thereon.

Powdery Preparation 1:

Salmon calcitonin (3 mg/3,000–3,500 MRC) was dissolved in an aqueous solution of pH 4.5 to pH 5.5 containing gelatin at a percentage of 1% and aspartic acid as a stabilizing agent at a percentage of 0.38%, and the resulting mixture solution was lyophilized. The lyophilized mixture was then admixed in an agate mortar with 200 mg of hydroxyapatite for 10 minutes, and 300 mg of hydroxyapatite was further added. The resulting mixture was stirred at humidity of 55% for 20 minutes. Further, 497 mg of hydroxyapatite was added and the mixture was admixed for 30 minutes at humidity of 55%, thereby yielding 1,000 mg of a powdery composition.

The mean particle size of hydroxyapatite used for the preparation is 50 μm.

A powdery preparation containing eel calcitonin was prepared in substantially the same manner as above, except for using eel calcitonin in place of salmon calcitonin.

Powdery Preparation 2:

Insulin (200 IU) was admixed in an agate mortar with 200 mg of hydroxyapatite for 10 minutes, and 300 mg of hydroxyapatite was further added. The resulting mixture was stirred at humidity of 55% for 20 minutes. Further, 497 mg of hydroxyapatite was admixed for 30 minutes at humidity of 55%, thereby yielding 1,000 mg of powdery composition of the present invention.

The mean particle size of hydroxyapatite used for the preparation is 50 μm.

As described hereinabove, the physiologically active peptide compositions according to the present invention allows the physiologically active peptides, which are unlikely or difficult to be orally administered, to be administered through a nasal route with high absorbability and without irritation.

In particular, when the composition in powdery form having the physiologically active peptide such as calcitonin or insulin dispersed in the carrier—hydroxyapatite—is administered through the nasal route, that is, when it is applied to the mucous membrane of the nasal cavity, the physiologically active peptide is well absorbed into the body to show high clinical effects.

What is claimed is:

1. A physiologically active peptide composition comprising a physiologically active peptide and hydroxyapatite, wherein said physiologically active peptide is calcitonin and a physiologically effective amount of said calcitonin is dispersed homogeneously in and adsorbed homogeneously onto hydroxyapatite having a mean particle size ranging from 20 μm to 250 μm.

2. A physiologically active peptide composition comprising a physiologically active peptide and hydroxyapatite, wherein said physiologically active peptide is insulin and a physiologically effective amount of said insulin is dispersed homogeneously in and adsorbed homogeneously onto hydroxyapatite having a mean particle size ranging from 20 μm to 250 μm.

3. A physiologically active peptide composition as claimed in claim 2, wherein said composition is nasally administrable in a powdery form.

4. A method for nasally administering a physiologically active peptide and hydroxyapatite, comprising nasally administering to a subject in need of such treatment a physiologically effective amount of said physiologically active peptide which is dispersed homogeneously in and adsorbed homogeneously onto said hydroxyapatite, said hydroxyapatite having a mean particle size from 20 μm to 250 μm.

5. A method as recited in claim 4, wherein said physiologically active peptide is calcitonin.

6. A method as recited in claim 4, wherein said physiologically active peptide is insulin.

7. A method as recited in claim 4, wherein aspartic acid is employed with said physiologically active peptide as a stabilizing agent.

* * * * *